US00PP34322P2

(12) United States Plant Patent
Moon

(10) Patent No.: US PP34,322 P2
(45) Date of Patent: Jun. 14, 2022

(54) ***ZELKOVA* TREE NAMED 'ZSMTF'**

(50) Latin Name: *Zelkova serrata*
Varietal Denomination: ZSMTF

(71) Applicant: Dwayne Moon, Washington, GA (US)

(72) Inventor: Dwayne Moon, Washington, GA (US)

( * ) Notice: Subject to any disclaimer, the term of this patent is extended or adjusted under 35 U.S.C. 154(b) by 0 days.

(21) Appl. No.: 17/235,531

(22) Filed: Apr. 20, 2021

(51) Int. Cl.
*A01H 5/00* (2018.01)
*A01H 6/00* (2018.01)

(52) U.S. Cl.
USPC ..... Plt./216

(58) Field of Classification Search
USPC ..... Plt./216
See application file for complete search history.

*Primary Examiner* — Karen M Redden
(74) *Attorney, Agent, or Firm* — Cassandra Bright

(57) ABSTRACT

A new and distinct *Zelkova serrata* tree named 'ZSMTF' is disclosed, characterized by uniquely dense foliage and a distinctive red Fall foliage color. Trees have been observed to have good heat tolerance in the Southern United States. The new variety is a *Zelkova* tree, typically used as an ornamental tree.

2 Drawing Sheets

Figure 1:
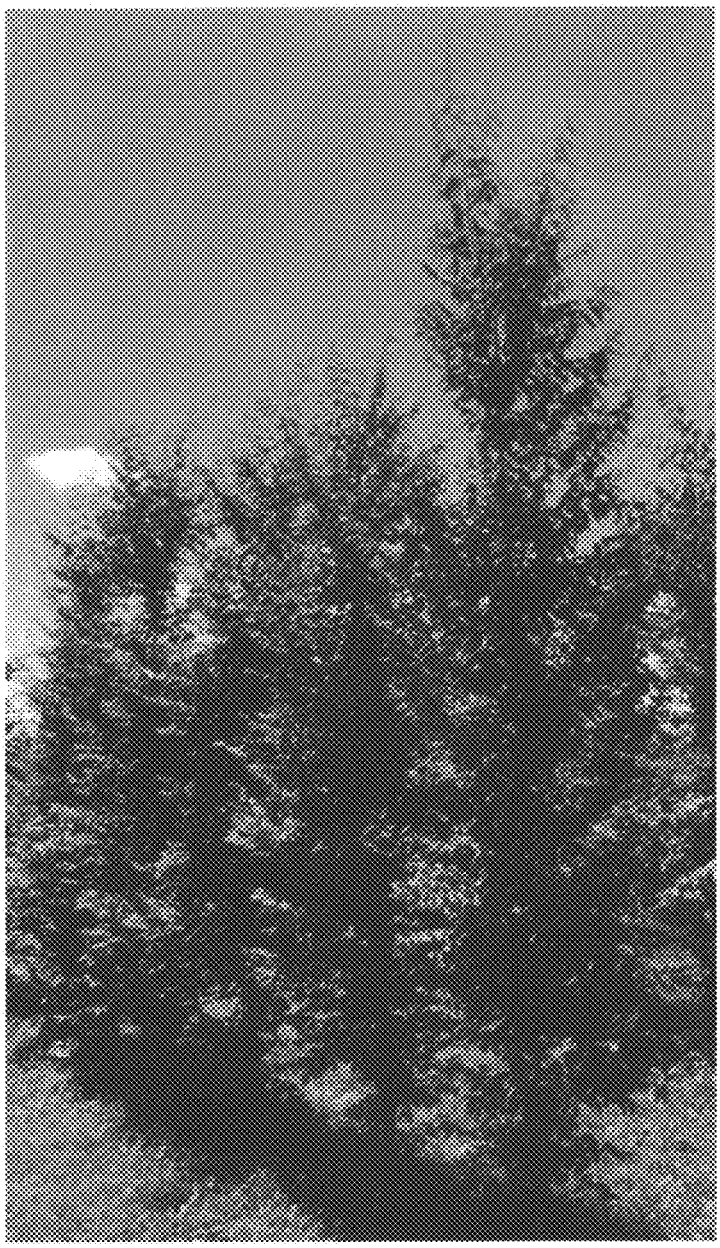

Latin name of the genus and species: *Zelkova serrata.*
Variety denomination: 'ZSMTF'.

BACKGROUND OF THE INVENTION

The new cultivar is a product of a planned breeding program. The new variety was discovered growing as a seedling among a group of crossbred *Zelkova serrata* trees at a tree farm in Washington, Ga. The inventor made this discovery in the Summer of 2016. The exact seed and pollen parents cannot be identified.

Asexual reproduction by grafting of the new cultivar 'ZSMTF' was first performed during January of 2017 at a farm in Washington, Ga. The cleft grafting system developed by the inventor has resulted in progeny that have proven the characteristics of the new variety to be genetically stable. This grafting process involved taking cuttings in February, being grafted, and being placed in calloused chambers for approximately three weeks. They are then moved into 3"×6" tree band pots and placed in humidity chambers for approximately four weeks. Furthermore, these observations have confirmed that the new variety represents a new and improved variety of *Zelkova serrata* tree as particularly evidenced by the superior heat tolerance. These genetic traits can be consistently reproduced by asexual propagation.

SUMMARY OF THE INVENTION

The cultivar 'ZSMTF' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'ZSMTF' grown in Washington, Ga. These characteristics in combination distinguish 'ZSMTF' as a new and distinct *Zelkova serrata* cultivar:

1. Dense foliage.
2. Red Fall foliage.
3. Good heat tolerance.

PARENT COMPARISON

The exact parent varieties cannot be identified.

COMMERCIAL COMPARISON

Plants of the new cultivar 'ZSMTF' are similar to plants of *Zelkova serrata* 'Green Vase', U.S. Plant Pat. No. 5,080, in most horticultural characteristics, however, plants of the new cultivar 'ZSMTF' differ in the following:

1. The new variety produces denser foliage than this comparator.
2. The new variety produces red Fall foliage; this comparator produces orange Fall foliage.
3. The new variety is more heat tolerant than this comparator.

Plants of the new cultivar 'ZSMTF' are similar to plants of *Zelkova serrata* 'Halka', U.S. Plant Pat. No. 5,687 in most horticultural characteristics, however, plants of the new cultivar 'ZSMTF' differ in the following:

1. The new variety produces smaller, denser foliage than this comparator.
2. The new variety produces red Fall foliage; this comparator produces yellow Fall foliage.
3. Trees of the new variety do not have the open, loose habit of this comparator.
4. The new variety is more heat tolerant than this comparator.

Plants of the new cultivar 'ZSMTF' are similar to plants of *Zelkova serrata* 'ZSFKF' U.S. Plant Pat. No. 17,220 in most horticultural characteristics, however, plants of the new cultivar 'ZSMTF' differ in the following:

1. The new variety produces smaller, denser foliage than this comparator.
2. The new variety produces red Fall foliage; this comparator produces greyed-orange Fall foliage.
3. Trees of the new variety do not have the open, loose habit of this comparator.

4. The new variety is more heat tolerant than this comparator.

Plants of the new cultivar 'ZSMTF' are similar to plants of *Zelkova serrata* 'Musashino' (unpatented) in most horticultural characteristics, however, plants of the new cultivar 'ZSMTF' differ in the following:

1. The new variety produces smaller, denser foliage than this comparator.
2. The new variety produces red Fall foliage; this comparator produces yellow Fall foliage.
3. The new variety is more heat tolerant than this comparator.

BRIEF DESCRIPTION OF THE PHOTOGRAPHS

The accompanying photograph in FIG. 1 illustrates a row of field trees of the new variety during early Summer.

Figure 2:
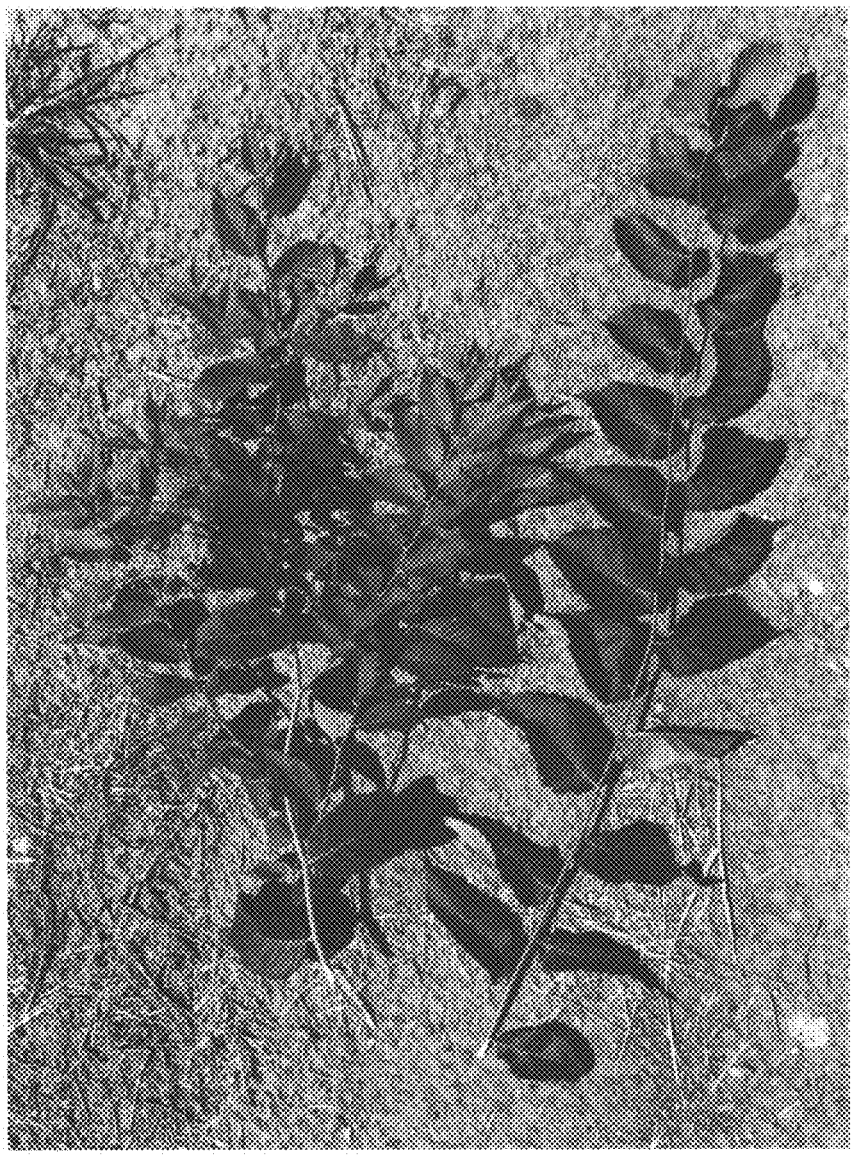

FIG. 2 illustrates a close-up view of the foliage, of the new variety and a comparator. Foliage of the new variety is on the left; foliage of the comparator 'ZSFK' is on the right.

All trees illustrated are field grown in Washington, Ga. Trees in FIG. 1 are approximately 3 years from planting into the field, 4 years old from grafting.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'ZSMTF' plants grown outdoors and in a nursery in Washington, Ga. Plants are approximately 2 years old, in a 3 gallon nursery container. Temperatures ranged from 5° C. to 10° C. at night to 18° C. to 27° C. during the day. Measurements and numerical values represent averages of typical plant types.

Botanical classification: *Zelkova serrata* 'ZSMTF'.

PROPAGATION

Cleft grafting.

Root description: Woody. Brown roots not accurately measured with an R.H.S. Colour Chart.

PLANT

Growth habit: Deciduous tree with a narrow canopy.

Height: Approximately 12 feet at 3 years.

Spread: Approximately 4 feet at 3 years.

Aspect and angle: About 45 degrees from center.

Growth rate: Rapid.

Trunk characteristics:

*Diameter*.—About 2.5 inches measured at approximately 3 inches above soil level at 3 years.

*Color*.—Near RHS Greyed-Green 198C blotched near Gray 201A.

*Surface texture*.—Rough, bark not yet formed.

*Lenticels present*.—Yes. Inconspicuous, round.

*Lenticel length*.—About 0.5 mm.

*Lenticel diameter*.—About 0.5 mm.

*Lenticel density*.—Very dense.

*Lenticel color*.—Near RHS Gray 201A.

Branch characteristics:

*Length*.—Average Range 30 to 65 cm.

*Diameter*.—Average 7 mm.

*Color*.—Near RHS Greyed-Green 197B.

FOLIAGE

Leaf:

*Leaf emergence*.—Mid-April in Georgia.

*Arrangement*.—Alternate.

*Shape*.—Broad Elliptic.

*Average length*.—Approximately 7 cm excluding petiole.

*Average width*.—Approximately 3 cm.

*Apex*.—Acuminate.

*Base*.—Rounded tapered.

*Margin*.—Serrate.

*Texture of top surface*.—Glabrous.

*Texture of lower surface*.—Glabrous.

*Color*.—Young foliage: Upper side: Near RHS Green 137C flushed Greyed-Orange N167C. Under side: Near RHS Yellow-Green 144A flushed Yellow-Green N144A. Mature foliage: Upper side: Near RHS Green 137A. Under side: Near RHS Green 137D. Fall foliage: Upper side: Near RHS Greyed-Red 180A, slightly flushed Red 53A. Under side: Near RHS Greyed-Red 180A.

*Venation*.—Type: Pinnate. Color(mature): Venation color upper side: Near RHS Yellow-Green 145B. Venation color under side: Near RHS Yellow-Green N144A.

*Petiole*.—Length: Average 5 to 9 mm. Diameter: Average 2 mm. Texture: Glabrous. Color: Upper side: Near RHS Yellow-Green N144C. Under side: Near RHS Yellow-Green 144C.

FLOWER

Not observed.

REPRODUCTIVE ORGANS

Not observed.

OTHER CHARACTERISTICS

Fruit/seeds: Not observed to date.

Disease/pest resistance: Neither resistance nor susceptibility to normal diseases and pests of *Zelkova* has been observed.

Drought resistance: No observed tolerance for drought to date. Typically *Zelkova* can become drought tolerant when well established.

Temperature tolerance: USDA Zones 5 through 8. Observed tolerant of hot Summer conditions in Georgia.

Fruits/nuts: Not observed.

What is claimed is:

1. A new and distinct cultivar of *Zelkova serrata* tree named 'ZSMTF' as herein illustrated and described.

* * * * *